United States Patent [19]

Kiel

[11] Patent Number: 4,871,770

[45] Date of Patent: Oct. 3, 1989

[54] METHOD OF INHIBITING THE ACTIVITY OF PEROXIDASES AND STIMULATING TUMOR GROWTH

[75] Inventor: Johnathan L. Kiel, San Antonio, Tex.

[73] Assignee: The United States of America as represented by the Secretary of the Air Force, Washington, D.C.

[21] Appl. No.: 133,675

[22] Filed: Dec. 16, 1987

Related U.S. Application Data

[60] Continuation of Ser. No. 652,370, Sep. 19, 1984, Pat. No. 4,766,150, which is a division of Ser. No. 251,694, Apr. 7, 1981, Pat. No. 4,486,408.

[51] Int. Cl.$^4$ ............................................. A61K 31/195
[52] U.S. Cl. .................................................... 514/567
[58] Field of Search ................................ 514/561, 567

[56] References Cited

PUBLICATIONS

Huang—J. Pharmacol Expl. Therapy, vol. 134, (1961) pp. 257–265.

Huang et al.—Chem. Abst., vol. 67 (1967) p. 9082u.

Primary Examiner—Sam Rosen
Attorney, Agent, or Firm—Stanton E. Collier; Donald J. Singer

[57] ABSTRACT

A composition and process for suppressing the immune system of animals in which an effective amount of 3-aminotyrosine is administered which suppresses the endogeneous immune system of animals. In addition endogeneous peroxidase activity is inhibited and tumor growth is stimulated.

1 Claim, No Drawings

METHOD OF INHIBITING THE ACTIVITY OF PEROXIDASES AND STIMULATING TUMOR GROWTH

STATEMENT OF GOVERNMENT INTEREST

The invention described herein may be manufactured and used by or for the Government for governmental purposes without the payment of any royalty thereon.

This application is a continuation of Ser. No. 652,370, filed Sept. 19, 1984, which is a divisional application of Ser. No. 251,694, filed Apr. 7, 1981, now U.S. Pat. No. 4,486,408. During the work leading to the invention disclosed and claimed in U.S. Pat. No. 4,766,150 it was discovered, for the first time, that administering an effective amount of 3-aminotyrosine suppressed the endogenous immune system of animals.

BACKGROUND OF THE INVENTION

This invention relates to biochemistry and more particularly to an enzymatic preparation for the control of tumor growth and immune diseases, and a process of administering said preparation to mammals.

This invention further relates to a process for suppressing the immune system of animals wherein an effective amount of 3-aminotyrosine is administered to animals for suppressing the endogenous immune system thereof.

Ample evidence has shown that the combination of certain peroxidases with hydrogen peroxide and a halide ion produces a system with strong cytotoxic properties. The myeloperoxidase-hydrogen peroxide-chloride system forms a potent cytotoxic system effective against bacteria, fungi, viruses, mycoplasma, and various mammalian cells. Similarly, the lactoperoxidase-hydrogen peroxide-thiocyanate system and the horseradish peroxidase-hydrogen peroxide-chloride system have been shown to have potent cytotoxic activities.

An equally cytotoxic system is obtained when instead of hydrogen peroxide, a hydrogen peroxide generating system is used. Thus, the glucose oxidase-horseradish peroxidase-chloride combination yields a potent cytotoxic system upon the addition of glucose. Galactose oxidase and xanthine oxidase have also been shown to be effective in this respect. Furthermore, we showed that the endogenous NADH oxidase activity of the horseradish peroxidase is also capable of promoting the cytotoxic activity of the enzyme in the presence of chloride ions.

A large body of evidence indicates that cytotoxic systems such as those described above may be operative in polymorphonuclear leukocytes, eosinophils, macrophages, and other cell types with cytotoxic properties. Such cells in general appear to utilize an NADH or NADPH oxidase as the peroxide-generating enzyme.

Macrophages are a necessary component in the augmentation of natural killer cell activity by Bacillus Calmette-Guerin (BCG) in mice. BCG also increases the peroxide and superoxide production by macrophages. The possibility thus exists that the peroxidase system of the macrophages plays a role in the augmentation of the natural killer cell activity. Similarly, peripheral lymphocytes, which are predominantly T-cells, contain a cytotoxic peroxidase. Chemiluminescence resulting from peroxide generating oxidative metabolism is observed when T lymphocytes are stimulated by Concanavalin A. Furthermore, immunization of mice with either soluble or particulate antigens causes an increase in peroxidase activity in the spleen which precedes the generation of specific antibody. These observations suggest that oxidase and/or peroxidase activity is in some way involved in developing specific immune responses.

Thus far none of the cytotoxic systems described above have been used in any in vivo experiments. However, some relevant experiments were done some time again by Schultz and his colleagues. Schultz, Synder, Wer, Berger and Bonner; Chemical Nature and Biological Activity of Myeloperoxidase: *Molecular Basis of Electron Transport*, Academic Press, New York, N.Y., pp. 301–321 (1972); and Schultz, Baker, and Tucker; Myeloperoxidase-Enzyme-Therapy of Rat Mammary Tumors; *Cancer Enzymology*, Academic Press, New York, N.Y. pp 319–334 (1976) Using mice bearing 20-methylcholanthrene induced tumors, these authors injected myeloperoxidase in combination with thio-TEPA, an antitumor drug. They observed a significant reduction in tumor growth in the treated mice, but no complete remissions. Neither myeloperoxidase nor thio-TEPA alone were effective in reducing tumor growth. The inhibition of tumor growth lasted as long as the treatment with myeloperoxidase and thio-TEPA was continued.

These results indicated that the activity of myeloperoxidase could play a role in the control of tumor growth, either directly or indirectly. Definite conclusions are difficult to obtain with such experiments, however, because the biological half-life of myeloperoxidase is only about 24 hours. It is noteworthy, that the toxic activity appeared to be specifically directed to the tumor tissue.

SUMMARY OF THE INVENTION

We have discovered that several peroxidases, when used in combination with a hydrogen peroxide and/or superoxide generating system, possess a potent cytotoxic activity toward eukaryotic cells when administered to tumor-bearing animals. We further discovered that this cytotoxic activity appears to be exclusively directed toward the neoplastic tissues.

In order to obtain the tumoricidal activity, it is necessary that the two enzymes be kept in close proximity to each other and that the enzymes be stabilized such as to significantly increase their in vivo half-life. Both these requirements can be met by immobilizing the enzymes, either separately or in combination, onto an insoluble support. This immobilization can be done by either chemically attaching the enzyme molecules onto the insoluble support or by entrapment of the enzyme molecules within the molecular matrix of the support.

For the purpose of this patent application immobilization is defined as the association of active protein molecules with an insoluble macromolecule by any means that prevents the protein molecules from moving away from the insoluble support.

An insoluble compound is defined as a compound that does not form a true solution in an aqueous medium at around physiological pH values; aqueous media being aqueous buffer media as well as any bodily fluids. Compounds that form colloidal solutions in the above mentioned aqueous media are considered to be insoluble compounds.

One or more injections of the immobilized enzyme conjugate described above into tumor-bearing animals results in a partial or total regression of the tumor tissue.

It is preferable that the material be injected into the tumor or proximal to the tumor; however primary tumors as well as metastasized tumors are subject to the cytotoxic action of the immobilized enzymes.

We further discovered that the immobilized enzyme systems act as potent activators of the specific immune response in tumor-bearing animals. This activation of the specific immune response therefore may all or in part be responsible for the regression of the tumors. Similarly, injection of potent inhibitors, namely 3-aminotyrosine, of the cytotoxic activity of the immobilized enzyme system results in a depression of the specific immune response and makes animals more susceptible to develop tumor growth.

The foregoing indicate that the immobilized enzyme system augments and/or activates the natural mechanism(s) that the body uses to eliminate transformed or foreign cells present in the body, whereas inhibitors of the cytotoxic system are able to inhibit this natural defense mechanism of the body against the growth of abnormal cells.

Accordingly, it is an object of this invention to provide a preparation (in the form of a composition of matter, e.g., a gel) and a process (i.e., a method) for the control of tumor growths and immune diseases in mammals, including humans.

It is another object of this invention to provide the aforesaid preparation and process whereby the enzymatic constituents thereof are destroyed very slowly by the mammalian host, unlike others used in the treatment of cancer in mammals.

It is still another object of this invention to prevent damage to normal tissue, either on a gross or microscopic level.

It is yet another object of this invention to provide a preparation and a process for the treatment of diverse tumor types, because of the broad-spectrum effect of the preparation.

It is a further object of this invention to enhance the immune response, rather than immunosuppress.

It is a still further object of this invention to provide for the treatment of advanced metastasized tumors.

It is a yet further object of this invention to provide an alternative to treatments with severe side effects.

It is a further object of this invention to provide a process for suppressing the immune system of animals by administering an effective amount of 3-aminotyrosine.

These objects of this invention, as well as other objects related thereto (e.g., eliminating the prior art necessity of injecting directly into the tumor), will become readily apparent after a consideration of the description of the invention.

DETAILED DESCRIPTION OF THE PREFERRED EMBODIMENT AND OF THE PROCESS

As a preliminary matter, it is to be noted that as a matter of convenience to the reader our inventive insoluble cross-linked cytotoxic oxidase-peroxidase system will be referred to hereinafter as "ICCOPS". In addition, it is also to be noted that three to four-week-old Sprague-Dawley rats were each injected intraperitoneally with 0.5 or 1.0 ml of Novikoff hepatoma suspension. The tumors were allowed to develop for 5 days or until ascites was evident. At this time some animals were sacrificed to establish the presence of tumor. The remaining tumor-bearing animals were then divided into test and control groups and treatment was initiated.

Preparation of ICCOPS

The crosslinked enzyme was prepared by dissolving 10 mg of horseradish peroxidase and 300 mg of bovine serum albumin or human serum albumin in a solution containing 2 ml glucose oxidase (2400 units) and 2.5 ml of 0.1M phosphate buffer, pH 6.9. Polymerization was initiated by adding 75 $\mu$l of 25% glutaraldehyde, a polymerizing agent to the enzyme solution. The mixture was incubated for at least 24 hours at 4° C. or until a gel was formed. The gel was soaked in 100 times its volume of distilled water. The water was decanted off and the gel was further washed with 100 more volumes of distilled water over a sintered glass filter. The gel was then frozen and lyophilized. The lyophilized gel was ground in a mortar with a pestle to a size that would pass through an 18 gauge hypodermic needle when swollen in phosphate buffered saline (PBS), pH 7.4. The powdered ICCOPS was stored at $-20°$ C. until used.

Peroxidase activity of immobilized enzyme

Oxidase and peroxidase activity was qualitatively determined by adding 1 mg of the immobilized enzyme system to 0.1% glucose in PBS, pH 7.4, containing 1.5 mg ABTS per ml. If the green solution turned blue within an hour, the oxidase and peroxidase were considered active.

Procedures for treatments of tumor-bearing rats

The basic procedure for treatment with ICCOPS required three consecutive days of treatment with 5 mg of the preparation suspended in 1 ml PBS, pH 7.4, containing 0.1% glucose. The suspension was injected into the abdominal cavity of rats bearing 5-day old tumors. Variations in the treatment regimens were used as indicated in the results which are described later herein.

Assay of the Cellular Immunological Response in Rats

A single-cell suspension was produced from the spleens by passage through a stainless-steel screen (Collector, Bellco Glass Co., Vineland, N.J.). The cells were washed once in Hank's Balanced Salt Solution (HBSS, Colorado Serum Co., Denver, Colo.), and then suspended in a Tris-ammonium chloride solution. The Tris-ammonium chloride solution was prepared from 10 ml 0.17 M Tris and 90 ml 0.16 M ammonium chloride and the solution was adjusted to pH 7.2. The suspension was incubated in a water bath at 37° C. to lyse the erythrocytes. The cells were centrifuged at 1000 rpm in a CRC 5000 DAMON/IEC Division centrifuge for 10 minutes and the supernatant was discarded. The cells were washed in HBSS and again centrifuged. The pellet was suspended in Modified Eagles Medium (Gibco, Grand Island, N.Y.) supplemented with 10% (V/V) normal rabbit serum (KC Biologicals, Linexa, Kans.), Hepes buffer 10 mM (Gibco), non-essential amino acids (Gibco) and penicillin-streptomycin. A 100 l aliquot of cells was withdrawn and mixed with 100 $\mu$l 0.4% trypan blue. After three minutes, the cells and dye mixture was diluted with 19.8 ml physiological saline solution - resulting in a 1:200 dilution of cells. The cells were counted in a hemocytometer and their concentration adjusted to $2 \times 10^6$ viable cells/ml. Viability was routinely greater than 90%.

The various antigens and mitogens were stored sterile at 4° C. dissolved in PBS, pH 7.2, at concentrations of 1 mg/ml, 100 μg/ml, and 10 μg/ml. Cultures were performed in standard 96-well microtiter plates constructed from tissue-culture quality plastic (Falcon Plastics, Los Angeles, Calif.). To the wells requiring antigen at 1 μg/ml, 10 μl of antigen at 10 μg/ml was added. To achieve final concentrations of 10 μg/ml or 100 μg/ml, for example, 10 μl of 100 g/mi or 1 mg/ml were added, respectively. Other concentrations of various mitogens were prepared in a similar manner. The specific antigen utilized was Keyhole Limpet Hemocyanin(KLH, Schwartz/Mann Laboratories, Orangeburg, N.Y.) with which the rats were inoculated subcutaneously 14 days prior to the introduction of tumor cells. Each rat received 200 μg of KLH in 0.1 ml PBS, pH 7.6. Concanavalin A (ConA) from Boehringer Mannheim (Indianapolis, Indiana) was the mitogen utilized in the assays. The negative control consisted of the addition of 10 μl of PBS at pH 7.2 to each control well. After the addition of antigen or mitogen, each well received 100 μl of the cell suspension. The plates were incubated at 37° C. in a humid atmosphere containing 5% $CO_2$ for 24 hours. Next, the wells were pulsed with 100 μl of MEM containing tritiated-thymidine at 5 μCi/ml, specific activity 2 Ci/mmol. After 48 hours of culture, the cells were harvested onto glass-fiber filters using a Titertech cell harvester (Flow Laboratories, McLean, Virginia). After drying, the filters were counted in a scintillation fluid consisting of toluene, PPO, and POPOP.

TEST RESULTS ATTAINED BY USE OF THE PREFERRED EMBODIMENT AND THE PROCESS

Regression of Novikoff Hepatomas in Rats

Young female Sprague-Dawley rats were intraperitoneally inoculated each with 0.5 ml of a Novikoff hepatoma cell suspension. Five days later the tumors had developed and in most cases ascites fluid was present in the peritoneal cavity. At this point each rat was injected intraperitoneally with 5 mg. ICCOPS suspended in a 1% glucose solution. The following day the rats were again given 5 mg ICCOPS, and this was repeated on the third day. Control experiments were done by injecting ICCOPS from which either the glucose oxidase or the peroxidase was omitted or by injecting only the glucose solution. Five days after the last treatment four of the seven animals treated with the complete ICCOPS system were sacrificed together with all the control animals that were still alive. All control animals had developed massive abdominal tumors amounting to as much as 25 grams of tumor tissue. The animals treated with the complete ICCOPS system, on the other hand, showed the presence of some yellow fibrous connective tissue, but no signs of active tumor growth. The three animals that were saved here remained alive for eight months with no apparent ill effects. (See Table I).

Thus far a total of 24 Novikoff hepatoma bearing rats have been treated with the complete ICCOPS system. A complete regression of the tumor tissue occurred in each one of the animals, and in all cases no apparent ill effects were present following the treatment.

TABLE I

| Remission of Novikoff Hepatoma tumors in Inoculated Rats | |
|---|---|
| Treatment | Remission |
| HRP-GOD-BSA (3 days) | 15/17 |
| HRP-BSA (3 days) | 0/2 |
| GOD-BSA (3 days) | 0/3 |
| LPO-GOD-BSA (5 days) | 4/4 |

TABLE I-continued

| Remission of Novikoff Hepatoma tumors in Inoculated Rats | |
|---|---|
| Treatment | Remission |
| None | 0/5 |

Effect on ICCOPS on Hepatoma Tumors

A young female rat was inoculated intraperitoneally with 0.5 ml of Novikoff hepatoma cell suspension and the tumor was allowed to develop for 5 days. At this point the abdominal cavity was opened under anesthesia. Typical tumor development was observed accompanied by ascites. The abdominal cavity was subsequently closed and 5 mg ICCOPS was injected i.p. The cavity was opened again under anesthesia 30 hours after the administration of ICCOPS. The rat was subsequently given 2 more doses of 5 mg ICCOPS on 2 consecutive days following the first administration, and the abdominal cavity was opened again on the 10th day after the last treatment. At this point the tumor was converted to a hard, nodular, yellow fibrous mass. The rat subsequently bred 2 months later and produced a normal litter. This experiment illustrated that the peroxidase promoted tumor regression occurs by means of tumor cell lysis. Most of the ICCOPS particles were found in the omental tissue. Apparently there is little or no direct contact between the ICCOPS particles and the tumor cells, suggesting that the cytotoxic activity of the ICCOPS particles is transferred to the tumor cells via one or more soluble intermediates.

Histopathological Analysis

A hematoxylin and eosin preparation of the actively growing Novikoff hepatoma was studied. The tumor cells appeared to be of epithelial origin and little connective tissue stroma or encapsulation was evident. The cells were poorly differentiated. The tumor consisted of a continuum of cells forming occasional small cystic appearing structures. The tissue showed an occasional limited differentiation towards pseudorosettes of the cells around the vasculature, and in some areas attempted differentiation towards a papillary pattern. Mitotic figures were common. Vascularity was limited and there were numerous areas of necrosis present in the tissue. The tumor was therefore designated an undifferentiated carcinoma with some characteristics of a papillary cystic adenocarcinoma.

The same preparation of the yellow remains of the tumor taken 10 days after the final treatment with ICCOPS was studied. The tissue consisted of islands of necrotic cells encapsulated by an active fibroblastic response. There was a marked collapse of the neoplastic tissue and necrosis appeared to be total. The tissue thus demonstrated tissue necrosis with secondary fibroplasia.

The mesenteric lymph nodes of the same animal showed disruption by an infiltration of neoplastic cells into the nodes. The neoplastic cells had started the formation of discrete islands of tissue, which is indicative of active neoplastic metastasis. Thus this animal had already suffered metastasis when the primary tumor was being destroyed. If this observation is representative of the other animals one can only conclude that any metastasized tumor was subsequently destroyed, since all remaining rats fully recovered.

Effect of Peroxidase Inhibitors

In order to obtain additional evidence that the observed tumor regression was indeed promoted by the ICCOPS system we did an experiment in which some animals were injected with a potent peroxidase inhibitor. The DOPA analog 3-aminotyrosine is a potent inhibitor of horseradish peroxidase with $K_1$ of 5 $\mu$M.

In this experiment we administered ICCOPS to 8 hepatoma-bearing rats. Four of the animals were also injected with 100 $\mu$g of 3-aminotyrosine.

The results indicated that the 3-aminotyrosine inhibited the action of ICCOPS and all 4 rats that received 3-aminotyrosine eventually died of the tumor, whereas the four rats receiving ICCOPS only showed complete remission. This confirms that the regression of the hepatomas is indeed promoted by the ICCOPS.

Effect of ICCOPS of Normal Tissue

Two of the male rats with regressed Novikoff hepatomas were sacrificed on the 10th day following the treatment with ICCOPS in order to evaluate the effects of the treatment on fast proliferating normal cells. For this purpose we examined the testes of the animals by electron microscopy and found that the sertoli cells and spermatogenesis appeared completely normal.

We also injected 100 mg of ICCOPS into 3 normal healthy animals on three consecutive days. On the fourth day one of the animals was sacrificed. Microscopic examination showed that the ICCOPS particles were again embedded in the omental tissue. The other two rats were kept alive for another 6 months. During this time we did not observe anything that distinguished them from any other normal healthy animal.

Effect of ICCOPS on Other Tumors

In order to determine whether or not the cytotoxic action of ICCOPS in vivo is specific for rat adenocarcinomas we tested the effect of ICCOPS on several types of tumors.

A malignant mouse melanoma (G16-F1) was grown in mice, and after an appreciable amount of tumor cells were present in the animals, treatment with ICCOPS was initiated. The results showed that tumor necrosis occurs as a result of the ICCOPS treatment. However, treatment for 4 to 5 consecutive days was necessary to obtain complete remission.

We also treated several spontaneous rat breast tumors. In these cases 5 mg ICCOPS was injected in the proximity of the tumor for 3 to 4 consecutive days. A biopsy, taken 10 days after the last day of treatment showed that complete remission of the tumor had occurred. Pathological examination revealed that both a spontaneous breast carcinoma and a breast sarcoma could successfully be treated with ICCOPS.

Furthermore we treated a dog with advanced Hodgkins's disease (a malignant lymphoma). ICCOPS was injected directly into one of the diseased lymp nodes for 3 days. At that point the dog died. However, severe necrosis of the lymphoma was observed in the treated lymph nodes, indicating that this lymphoma is also sensitive to the action of ICCOPS.

Finally, in a similar manner we achieved a complete remission of a benign tumor (a fibroadenoma) in a rat.

These data indicate that at least several types of tumors are affected by the cytotoxic activity of ICCOPS, and animals bearing such tumors can successfully be treated in this manner. Our data indicate, however, that no all tumors respond equally well to ICCOPS treatment; a different treatment schedule is required for each type of tumor in order to achieve complete remission.

Antitumor Activity of Other Peroxidases

Substitution of lactoperoxidase for horseradish peroxidase in the ICCOPS preparation yields a product that is also effect in promoting tumor regression in vivo. Its in vivo activity toward rat hepatomas is somewhat less than that of the horseradish peroxidase system; administration had to be carried out for 4 consecutive days to achieve the same results as with 3 days of ICCOPS administration.

These results show that the tumoricidal activity is not specific for the horseradish peroxidase but can also be promoted by certain other mammalian peroxidases.

Enchancement of Tumor Growth by Aminotyrosine

In order to evaluate whether or not endogenous peroxidases play a role in the natural resistance to neoplastic growth we injected some rats with a potent inhibitor of the cytotoxic activity of peroxidases and subsequently challenged the animals with a suspension of hepatoma cells.

Four adult male rats were injected i.p. with 1 mg of 3-aminotyrosine in 1 ml of water. Four control rats were injected with 1 ml of water. The following day all rats were injected with 1 ml of a dilute Novikoff hepatoma cell suspension; the number of cells being normally insufficient to produce tumor growth. On the same day an additional 1 mg aminotyrosine was administered to the rats that received the inhibitor the previous day and this was repeated for 3 more days. The four control rats similarly received water injections.

On the ninth day following the inoculation with tumor all rats were sacrificed and examined for the presence of tumor. No tumor was present in any of the control animals. On the other hand, each of the animals that were treated with aminotyrosine had developed tumor growth. One rat had a large central omental tumor, whereas the other three rats contained a number of small tumors scattered through the mesenteric omentum and over the surface of the small intestines.

This dramatic difference indicates that 3-aminotyrosine inhibits the natural mechanism by which the animal protects itself against neoplasia. As such its action is similar to that of various immune suppressant compounds.

Effects of ICCOPS on the Immune System

Table II illustrates the change in response to Concanavalin A stimulation of spleen cells obtained from tumor-bearing rats and from rats with regressed tumors as compared to normal healthy animals. The data show that spleen cells from tumor-bearing animals are highly active in incorporating thymidine and are insensitive to further stimulation by Concanavalin A. In fact, even at low concentrations the mitogen acts as an inhibitor. Spleen cells obtained from animals with regressed tumors, on the other hand, can be stimulated by the mitogen, even though they are more active than the cells from healthy rats.

When spleen cells from animals with actively regressing tumors were tested, we observed a pattern similar to that of animals with completely regressed tumors. These results suggest that the changes in the immune response occur soon after the administration of ICCOPS. Similar results were obtained with spleen cells of rats previously immunized with KLH. (Table III). Again, the cells of animals with actively regressing tumors behaved more like cells from normal animals in their response to stimulation with KLH than like cells from tumor-bearing animals.

These data indicate that changes in the immune system occur concomitantly with the tumor regression as a result of the action of the peroxidase system. Whether these changes occur as a result of the regressing tumor or are directly caused by the presence of the peroxidase system cannot be ascertained at the present time.

TABLE II

Responses of Rat Spleen Cells to Concanavalin A in Tumor-Bearing Rats and Rats with Regressing Tumors (5 days after Treatment)

| Con A | Normal Rats CPM$^a$ | SI$^b$ | Tumor-Regressing Rats CPM | SI | Tumor-Bearing Rats CPM | SI |
|---|---|---|---|---|---|---|
| 0 | 1165 ± 34 | 1.0 | 6341 ± 1266 | 1.0 | 23343 ± 284 | 1.0 |
| 1 μg | 1409 ± 34 | 1.2 | 10062 ± 946 | 1.6 | 25357 ± 817 | 1.0 |
| 10 μg | 2627 ± 127 | 2.2 | 12854 ± 1203 | 2.0 | 23084 ± 482 | 0.98 |
| 50 μg | 3130 ± 860 | 2.7 | 3028 ± 214 | 0.48 | 17970 ± 3855 | 0.77 |
| 100 μg | 1346 ± 36 | 1.2 | 1833 ± 832 | 0.29 | 2150 ± 813 | 0 |

$^a$CPM of tritiated-thymidine taken up by $2 \times 10^5$ cells ± the standard deviation for 3 samples.
$^b$SI = Stimulation index: mitogen induced response divided by the control response without mitogen.

TABLE III

The Specific Immune Response (Secondary) to KLH by Spleen Cells from Normal, Tumor-Regressing, and Tumor-Bearing Immunized Rats

| KLH | Normal Rats CPM | SI* | Tumor-Regressing Rats CPM* | SI | Tumor-Bearing Rats CPM | SI |
|---|---|---|---|---|---|---|
| 0 | 386 ± 62 | 1.0 | 3864 ± 61 | 1.0 | 18295 ± 122 | 1.0 |
| 1 μg | 557 ± 57 | 1.4 | 3967 ± 688 | 1.0 | 10288 ± 387 | 0.6 |
| 10 μg | 1973 ± 407 | 5.1 | 6705 ± 600 | 1.7 | 10712 ± 115 | 0.6 |
| 100 μg | 598 ± 118 | 1.5 | 6501 ± 359 | 1.7 | 13442 ± 226 | 0.7 |

*The stimulating index (SI) and the mean CPM ± 5.0, were determined as in Table II.

CONCLUSION

It is abundantly clear from all of the foregoing that the stated objects of this invention, as well as objects related thereto, have been achieved.

The data presented in this application shows that ICCOPS, an immobilized system with glucose oxidase and horseradish peroxidase as its functional components, rapidly and selectively destroys a very malignant and advanced adenocarcinoma in rats. In addition, other malignant tumors, including a melanoma, a sarcoma and a lymphoma, are subject to selective destruction by ICCOPS. Previous in vitro studies by others using soluble glucose oxidase and horseradish peroxidase showed no specificity for tumor cells as compared with normal cells. A similar lack of specificity was observed with the myeloperoxidase and lactoperoxidase systems. In our in vivo study, on the other hand, a very high degree of selectivity was obtained as illustrated by two facts. Firstly, no obvious damage was found to normal tissues, including to rapidly proliferating testicular cells; and secondly, the histopathological tissue slices show that fibroblasts located adjacent to necrosing tumor cells are essentially normal.

We also demonstrated that peroxidases other than horseradish peroxidase can be used in ICCOPS. Tumor regression has been obtained using the lactoperoxidase and cytotoxic activity in vitro was demonstrated using myeloperoxidase and snake skin peroxidase.

The function of the glucose oxidase in the ICCPS system is merely to provide the hydrogen peroxide and/or superoxide needed to convert the peroxidase into the cytotoxic form. Glucose oxidase was chosen for reasons of convenience, since its substrates (glucose and oxygen) are readily available for its in vivo use. However, its function can be fulfilled by any enzyme for example xanthine oxidase, that produces either hydrogen peroxide or superoxide.

We also found that the peroxidase system activates a secondary antitumor mechanism. This secondary system appears to be the cell-mediated portion of the immune system. The spontaneous blastogenic activity of spleen cells of rats with actively growing tumor indicates a maximally stimulated immune system that fails to produce an effective response. Introduction of ICCOPS, however, rapidly modifies the immune system by reducing the ineffective response and restoring the mitogenic and specific immune response. These results indicate that ICCOPS acts as an immunostimulant in animals whose normal response is insufficient. The increased sensitivity of animals toward a challenge with tumor cells as a result of 3-aminotyrosine administration, thus acting as an immunosuppressant, also supports this conclusion. Hence, ICCOPS as well as peroxidase inhibitors could also be useful as therapeutic agents in diseases affecting the immune system, in regulating the immune system following organ transplants, and other tissue implantations, as well as in any therapy that requires either a suppression or activation of the endogenous immune response.

There are, of course, many variations to the specific steps, techniques, dosage, materials, and the like, used in our work described herein.

Additionally, all equivalents to the preferred embodiment expressly described herein are intended to be encompassed within the following claims.

What is claimed is:

1. A method of inhibiting the activity of the endogenous peroxidases and stimulating tumor growth comprising administering an effective amount of 3-aminotyrosine to a mammal to thereby stimulate tumor growth.

* * * * *